United States Patent [19]
Hamilton, Jr.

[11] Patent Number: 5,171,914
[45] Date of Patent: Dec. 15, 1992

[54] DEHYDROGENATION CATALYST AND PROCESS

[75] Inventor: David M. Hamilton, Jr., Houston, Tex.

[73] Assignee: Shell Oil Company, Houston, Tex.

[21] Appl. No.: 752,301

[22] Filed: Aug. 30, 1991

[51] Int. Cl.$^5$ .................. C07C 5/333; B01J 23/74; B01J 23/78

[52] U.S. Cl. .................. 585/444; 502/326; 585/445

[58] Field of Search ............... 585/444, 445; 502/326

[56] References Cited

U.S. PATENT DOCUMENTS

| | | | |
|---|---|---|---|
| 3,364,277 | 1/1968 | Siem | 260/680 |
| 3,703,593 | 11/1972 | Turley et al. | 252/470 |
| 3,904,552 | 9/1975 | O'Hara | 252/458 |
| 4,098,723 | 7/1978 | Riesser | 252/474 |
| 4,152,300 | 5/1979 | Riesser | 252/462 |
| 4,467,046 | 8/1984 | Smith et al. | 502/174 |
| 4,560,819 | 12/1985 | Chu | 585/444 |
| 4,720,604 | 1/1988 | Chu | 585/444 |
| 4,857,498 | 8/1989 | Dejaifve et al. | 585/444 |

OTHER PUBLICATIONS

Bishop, "Micaceous Iron Oxide Pigments", J. Oil Col. Chem. Assoc., vol. 64, pp.57-74, 1981.

*Primary Examiner*—Asok Pal

[57] ABSTRACT

The instant invention relates to an improved dehydrogenation catalyst made up of iron oxide and potassium oxide which has been prepared by combining an iron-containing compound made up of from about 10% to 100% by weight of a micaceous iron oxide and a potassium-containing compound to form a pellet, followed by calcination. The catalyst is particularly suited for the non-oxidative dehydrogenation in the presence of steam of ethylbenzene to styrene.

18 Claims, No Drawings

DEHYDROGENATION CATALYST AND PROCESS

BACKGROUND OF THE INVENTION

1. Field of the Invention

The present invention relates to catalysts and processes for the non-oxidative dehydrogenation of hydrocarbons in the presence of steam to corresponding more-unsaturated hydrocarbons, particularly to the production of styrene from ethylbenzene.

2. Background

Potassium oxide-modified iron oxide based catalysts have long been used to non-oxidatively dehydrogenate hydrocarbons. In addition to the potassium oxide, other metals have been used to modify these iron-based catalysts; e.g., V, Co as noted in U.S. Pat. No. 4,098,723, issued Jul. 4, 1978; Mo, Ca, Cr as noted in U.S. Pat. No. 4,467,046, issued Aug. 21, 1984; Al, Cd, Mg, Mn, Ni, U, rare earths as noted in U.S. Pat. No. 4,152,300; and Sc, Y, La, Zn, W as noted in European Patent Publication 195,252, published Jan. 1, 1991.

Various types of iron oxides have been used to prepare these dehydrogenation catalysts, including the so-called red, yellow and black forms. The yellow iron oxide is usually geothite, which is the common form of hydrated iron oxide, $FeO(OH)$. The black form is magnetite, $Fe_3O_4$. The red form is the anhydrous form or hematite, $Fe_2O_3$. The red form is typically prepared by calcining the yellow form to drive off the water. This calcination of the yellow iron oxide produces red iron oxide having an acicular, or needle shape. Acicular hydrated iron oxide can also be produced by direct precipitation. U.S. Pat. No. 3,364,277, issued Jan. 16, 1968, teaches the use of yellow iron oxides to prepare dehydrogenation catalysts. U.S. Pat. No. 3,703,593, issued Nov. 21, 1972, teaches the use of mixtures of red and yellow iron oxides to prepare dehydrogenation catalysts. U.S. Pat. No. 3,904,552, issued Sep. 9, 1975, specifically teaches the use of acicular (needle) form of iron oxide (example 4) to prepare dehydrogenation catalysts.

Micaceous iron oxide is a hematite material that occurs in a tabular crystal form which can be fractured to give very thin platelets or lamellar fragments. Since its crystal structure is similar to that of mica, it has been termed "micaceous". It has been used in the preparation of protective paints. See for example Bishop, "Micaceous Iron Oxide Pigments", *J. Oil Col. Chem. Assoc.; Transactions and Communication*, 64, 57–74, 1981. It has now been found that the use of a micaceous iron oxide in the preparation of potassium oxide-modified iron oxide dehydrogenation catalysts results in catalysts with enhanced selectivities.

SUMMARY OF THE INVENTION

The instant invention relates to a dehydrogenation catalyst comprising iron oxide and potassium oxide which has been prepared by combining an iron-containing compound and a potassium-containing compound to form a pellet, followed by calcination, the improvement which comprises using an iron-containing compound consisting of from about 10 percent to about 100 percent by weight, basis $Fe_2O_3$, of a micaceous iron oxide. The catalyst is particularly suited for the non-oxidative dehydrogenation in the presence of steam of ethylbenzene to styrene.

DESCRIPTION OF THE PREFERRED EMBODIMENTS

This invention relates to a process for the preparation of a compound having the general formula:

wherein $R^1$ and $R^2$ each represent an alkyl, an alkenyl or a phenyl group or a hydrogen atom, by non-oxidative dehydrogenation of a compound having the general formula:

Wherein $R^1$ and $R^2$ have the same meaning as in formula I, in which process a mixture comprising a compound of formula II and super-heated steam is contacted at elevated temperature with a catalyst comprising iron oxide and potassium oxide which has been prepared by combining an iron-containing compound and a potassium-containing compound to form a pellet, followed by calcination, wherein in preparing the catalyst there was used as at least part of the iron-containing compound from about 10 percent to about 100 percent by weight, basis $Fe_2O_3$, of a micaceous iron oxide. The invention also relates to the improved catalysts.

$R^1$ in the general formula II may represent a phenyl group carrying one of more methyl groups as substituents. Preferably, $R^1$ represents an unsubstituted phenyl group and $R^2$ a hydrogen atom or a methyl group. Very good results have been obtained with ethylbenzene as the starting compound. The alkanes of Formula II preferably have in the range of from 2 to about 20 and particularly about 3 to about 8 carbon atoms per molecule; examples are n-butane and 2-methylbutane. The alkenes of formula II preferably have in the range of from about 4 to about 20 and particularly about 4 to about 8 carbon atoms per molecule; examples are 1-butene (forming 1,3-butadiene) and 2-methyl-1-butene and 3-methyl-1-butene, both forming isoprene. It is possible to convert n-butane with the present process via 1-butene into 1,3-butadiene and 2-methylbutane via tert.-amylenes into isoprene.

Preferred compounds of formula I which can be produced by the instant process are butadiene, alpha methyl styrene and styrene. The use of the instant catalysts to convert ethylbenzene to styrene is particularly advantageous in that the conversion is made with high selectivity.

A non-oxidative dehydrogenation is a dehydrogenation whereby no molecular oxygen is added.

The term "selectivity" as utilized herein is defined as the amount of compound of formula II that has been converted into compound of formula I divided by the total amount of compound of formula II that has been converted times one hundred. In the instant specification selectivities are typically measured at a standard rate of conversion of compound of formula II. For example, as used herein S(70) refers to the molar selectivity of ethylbenzene to styrene at a 70% molar conversion of ethylbenzene. The activity of a catalyst is inversely related to the temperature. The more active the catalyst, the lower is the temperature that will be needed to obtain the same rate of conversion. Activities utilized in the instant specification are typically related to a given rate of conversion. For example, T(70) refers to the temperature at which a 70% molar conversion of ethylbenzene occurs.

The process is suitably carried out using a molar ratio of steam to compound of formula II in the range of from about 2 to about 20 and preferably of from about 5 to about 13. The process is suitably carried out at a temperature in the range of from about 400° C. to about 750° C., preferably in the range of from about 550° C. to about 650° C. The process may be carried out at atmospheric, super- or sub-atmospheric pressure. Atmospheric or near atmospheric pressure is usually very suitable. The process is suitably carried out using a liquid hourly space velocity in the range of from about 0.1 to abut 5.0 l/l/hr, using, for example, a tubular or radial flow reactor.

The catalyst may be used in the form of, for example, pellets, tablets, spheres, pills, saddles, trilobes, tetralobes and the like. The catalyst generally comprises about 5 to about 20 percent by weight of potassium oxide, from zero to about 10 percent by weight of oxides of one or more promoter metals selected from the group consisting of Sc, Y, La, rare earth, Mo, W, Ca, Mg, V, Cr, Co, Ni, Mn, Cu, Zn, Cd, Al, Sn, Bi and mixtures thereof and the balance of ferric oxide. Preferred promoter metals are selected from the group consisting of Ca, Mg, Mo, W, Ce and mixtures thereof. The use of the term "oxide" herein is meant to encompass not only the single oxides, such as ferric oxide, but also mixtures of oxides such as spinels and ferrites as well as binary and other oxide mixtures. Under reaction conditions these oxides may be present in part in the form of oxidic compounds such as carbonates and bicarbonates.

The catalysts of this invention are compounded in a variety of ways, but basically they are prepared by admixing together iron-containing and potassium-containing compounds which are oxides or which convert to oxides upon calcining, forming this mixture into catalyst-sized particles and calcining at elevated temperature to form a durable particle. Promoter metal-containing compounds which are oxides or which also decompose to oxides upon calcination may be admixed with the iron-containing and potassium-containing compounds. The iron-containing, potassium-containing and promoter metal-containing compounds can also be denoted as oxide-providing compounds and may comprise, for example, oxides, carbonates, bicarbonates, nitrates and the like.

The catalysts are prepared with art recognized procedures. One method is to ball mill together a mixture of oxides/hydroxides/carbonates, etc., of iron, potassium and one or more optional promoter metals, adding a small amount of water, and extruding the paste to form small pellets, which are then dried at about 100° C. to about 300° C. and calcined at temperatures above 500° C., preferably between about 700° C. and about 1000° C. Another method is to dissolve the components together, or make a slurry and spray dry the resultant material to form a powder, calcine the powder into the resultant oxides, and then add sufficient water to from a paste and extrude into pellets, dry and calcine. Another procedure involves precipitation of those materials which are precipitable such as iron, as the resultant hydroxides, partially dewatering the resultant precipitate, adding soluble salts, for example, of potassium and promoter metals like calcium and magnesium, and then subsequently extruding, drying and calcining the extrudate. A pellet mill or pellet press could also be used to form the pellets. A preferred method is to first dry mix the powdered components and then mull these components with sufficient water to provide an extrudable mass. After mulling, the mixture is extruded, dried and calcined.

In general terms, after the components have been formed into a catalyst particle, the particle is calcined at elevated temperature to form a durable particle. The calcining temperature will be greater than about 500° C., preferably between about 700° C. and about 1000° C. Calcining atmospheres will generally be neutral, e.g., nitrogen, or oxidizing, such as oxygen or preferably air.

The iron oxide-providing compound that is used in the preparation of the instant catalyst will be a micaceous iron oxide that comprises from about 10 to 100 percent by weight of the total iron oxide-providing compound used, basis $Fe_2O_3$. The balance of the iron oxide-providing compound can be any other iron compound, and may include yellow, black and red iron oxides. Preferably this balance of iron oxide-providing compound is selected from the group consisting of goethite, hematite, magnetite, maghemite, lepidocrocite and mixtures thereof, and it most preferably is an acicular iron oxide. The use of the micaceous iron oxides in the preparation provides for catalysts which have enhanced selectivities for the conversion of ethylbenzene to styrene. The micaceous iron oxide used will preferably have a maximum platelet dimension of less than about 100 microns, more preferably less than about 25 microns, and most preferably less than about 10 microns.

Micaceous iron oxides are available from commercial suppliers of pigment grade iron oxides. Methods of preparing micaceous iron oxides are also found in the patent literature. See for example European Patent Application 307,486, filed Feb. 13, 1984; U.S. Pat. No. 3,864,463, issued Feb. 4, 1975; U.S. Pat. No. 3,987,156, filed Oct. 19, 1976; and U.S. Pat. No. 4,624,845, issued Nov. 25, 1986, all incorporated by reference herein.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The invention will be described by the following examples which are provided for illustrative purposes and are not to be construed as limiting the invention.

Catalyst Preparation

The following examples illustrate preparation of catalysts according to the invention as well as a comparative catalyst.

Comp Catalyst: This catalyst was prepared by combining the following catalyst components as a dry mixture: 1105 g of acicular red iron oxide (from Bayer AG, Germany, needle size 0.5–1 microns), 245 g of $K_2CO_3$, 120 g of $Ce_2(CO_3)_3*xH_2O$, 39 g of $(NH_4)_{10}W_{12}O_{41}*5-H_2O$ and 25 g of $CaCO_3$. This mixture was then mulled continuously for 25 minutes. The mulling procedure was as follows: 1) dry mull for the first 10 minutes, 2) add 217 ml of deionized water over the course of the next 5 minutes and 3) wet mull for the final 10 minutes.

The mulled material was pelletized in a commercial pellet mill. The wet pellets were dried at 170° C. for 1 hour and then calcined at 825° C. in air for 1 hour to produce the finished product.

Catalyst A: This catalyst was prepared by combining the following catalyst components as a dry mixture: 275 g of synthetic micaceous iron oxide (Laminox S from Cookson Laminox Ltd, England, platelet size less than 10 microns), 830 g of acicular red iron oxide (from Bayer AG, Germany, needle size 0.5–1 microns), 245 g of $K_2CO_3$, 120 g of $Ce_2(CO_3)_3 \cdot xH_2O$, 39 g of $(NH_4)_{10}W_{12}O_{41} \cdot 5H_2O$ and 25 g of $CaCO_3$. This mixture was then mulled continuously for 25 minutes. The mulling procedure was as follows: 1) dry mull for the first 10 minutes, 2) add 140 ml of deionized of water over the course of the next 5 minutes and 3) wet mull for the final 10 minutes. The mulled material was pelletized in a commercial pellet mill. The wet pellets were dried at 170° C. for 1 hour and then calcined at 825° C. in air for 1 hour to produce the finished product.

Catalyst B: This catalyst was prepared by combining the following catalyst components as a dry mixture: 552 g of synthetic micaceous iron oxide (Laminox S from Cookson Laminox Ltd, England, platelet size less than 10 microns), 552 g of acicular red iron oxide (from Bayer AG, Germany, needle size 0.5–1 microns), 245 g of $K_2CO_3$, 120 g of $Ce_2(CO_3)_3 \cdot xH_2O$, 39 g of $(NH_4)_{10}W_{12}O_{41} \cdot 5H_2O$ and 25 g of $CaCO_3$. This mixture was then mulled continuously for 25 minutes. The mulling procedure was as follows: 1) dry mull for the first 10 minutes, 2) add 140 ml of deionized of water over the course of the next 5 minutes and 3) wet mull for the final 10 minutes. The mulled material was pelletized in a commercial pellet mill. The wet pellets were dried at 170° C. for 1 hour and then calcined at 825° C. in air for 1 hour to produce the finished product.

Catalyst C: This catalyst was prepared by combining the following catalyst components as a dry mixture: 1508 g of synthetic micaceous iron oxide (Laminox S from Cookson Laminox Ltd, England, platelet size less than 10 microns), 502 g of acicular red iron oxide (from Bayer AG, Germany, needle size 0.5–1 microns), 446 g of $K_2CO_3$, 217 g of $Ce_2(CO_3)_3 \cdot xH_2O$, 71 g of $(NH_4)_{10}W_{12}O_{41} \cdot 5H_2O$ and 45 g of $CaCO_3$. This mixture was then mulled continuously for 25 minutes. The mulling procedure was as follows: 1) dry mull for the first 10 minutes, 2) add 217 ml of deionized of water over the course of the next 5 minutes and 3) wet mull for the final 10 minutes. The mulled material was pelletized in a commercial pellet mill. The wet pellets were dried at 170° C. for 1 hour and then calcined at 825° C. in air for 1 hour to produce the finished product.

Catalyst D: This catalyst was prepared in the same manner as Catalsyt C except that it was calcined at 775° C.

Catalyst E: This catalyst was prepared by combining the following catalyst components as a dry mixture: 2005 g of synthetic micaceous iron oxide (Laminox S from Cookson Laminox Ltd, England, with platelet size less than 10 microns), 446 g of $K_2CO_3$, 217 g of $Ce_2(CO_3)_3 \cdot xH_2O$, 71 g of $(NH_4)_{10}W_{12}O_{41} \cdot 5H_2O$ and 45 g of $CaCO_3$. This mixture was then mulled continuously for 25 minutes. The mulling procedure was as follows: 1) dry mull for the first 10 minutes, 2) add 165 ml of deionized of water over the course of the next 5 minutes and 3) wet mull for the final 10 minutes. The mulled material was pelletized in a commercial pellet mill. The wet pellets were dried at 170° C. for 1 hour and then calcined at 825° C. in air for 1 hour to produce the finished product.

Catalyst Testing

The above catalysts were tested under isothermal conditions in a standard pilot plant reactor designed for continuous operation. The conditions of the catalyst tests were as follows: 100 $cm^3$ of catalyst, 600° C. reactor temperature, liquid hourly space velocity of 0.65 measured in liters of ethylbenzene per liter of catalyst per hour, a steam to ethylbenzene molar ratio of 10:1 and a reactor pressure of 0.75 atmospheres.

The catalyst testing results are reported in terms of T(70) and S(70) where T(70) is the temperature required for a given catalyst to convert 70% of the ethylbenzene feed to styrene and S(70) is the molar selectivity to product styrene. Catalyst testing results are shown in Table 1:

TABLE 1

| TESTING RESULTS | | | | |
|---|---|---|---|---|
| | Calcine Temp | T(70) | S(70) | MIO[1] | ARIO[2] |
| Comp Catalyst | 825° C. | 599.9° C. | 95.0% | 0 | 100% |
| Catalyst A | 825° C. | 599.0° C. | 95.5% | 27% | 83% |
| Catalyst B | 825° C. | 599.6° C. | 96.1% | 50% | 50% |
| Catalyst C | 825° C. | 602.7° C. | 96.3% | 75% | 25% |
| Catalyst D | 775° C. | 598.0° C. | 96.3% | 75% | 25% |
| Catalyst E | 825° C. | 600.5° C. | 96.5% | 100% | 0 |

[1] Micaceous iron oxide, listed as weight percent of total iron oxide used in catalyst preparation, basis $Fe_2O_3$.
[2] Acicular red iron oxide, listed as weight percent of total iron oxide used in catalyst preparation, basis $Fe_2O_3$.

What is claimed is:

1. In a dehydrogenation catalyst comprising iron oxide and potassium oxide which has been prepared by combining an iron-containing compound and a potassium-containing compound to form a pellet, followed by calcination, the improvement which comprises using an iron-containing compound consisting of from about 10 percent to about 100 percent by weight, basis $Fe_2O_3$, of a micaceous iron oxide.

2. The catalyst of claim 1 wherein the micaceous iron oxide has a maximum platelet dimension of less than about 100 microns.

3. The catalyst of claim 2 wherein the micaceous iron oxide has a maximum platelet dimension of less than 25 microns.

4. The catalyst of claim 3 wherein the micaceous iron oxide has a maximum platelet dimension of less than about 10 microns.

5. The catalyst of claim 1 wherein the balance of the iron-containing compound which is not a micaceous iron oxide is selected from goethite, hematite, magnetite, maghemite, lepidocrocite and mixtures thereof.

6. The catalyst of claim 1 wherein the balance of the iron-containing compound which is not a micaceous iron oxide is an acicular iron oxide.

7. The catalyst or claim 1 which additionally comprises one or more oxides of a promoter metal selected from the group consisting of Sc, Y, La, rare earth, Mo, W, Ca, Mg, V, Cr, Co, Ni, Mn, Cu, Zn, Cd, Al, Sn, Bi and mixtures thereof with one or more of a promoter metal-containing compound being combined with the iron-containing compound and the potassium-containing compound.

8. The catalyst of claim 7 wherein the promoter metal is selected from Ca, Mg, Mo, W, Ce and mixtures thereof.

9. The catalyst of claim 1 wherein the calcination takes place at a temperature ranging from about 750° C. to about 1000° C.

10. In a process for the preparation of styrene by the non-oxidative dehydrogenation of ethylbenzene by contacting ethylbenzene and steam at a temperature ranging from about 500° C. to about 700° C. with a dehydrogenation catalyst comprising iron oxide and potassium oxide which has been prepared by combining an iron-containing compound and a potassium-containing compound to form a pellet, followed by calcination, the improvement which comprises using a catalyst prepared from an iron-containing compound consisting of from about 10 percent to about 100 percent by weight, basis $Fe_2O_3$, of a micaceous iron oxide.

11. The process of claim 10 wherein the micaceous iron oxide has a maximum platelet dimension of less than about 100 microns.

12. The process of claim 11 wherein the micaceous iron oxide has a maximum platelet dimension of less than 25 microns.

13. The process of claim 12 wherein the micaceous iron oxide has a maximum platelet dimension of less than about 10 microns.

14. The process of claim 10 wherein the balance of the iron-containing compound which is not a micaceous iron oxide is selected from goethite, hematite, magnetite, maghemite, lepidocrocite and mixtures thereof.

15. The catalyst of claim 10 wherein the balance of the iron-containing compound which is not a micaceous iron oxide is an acicular iron oxide.

16. The process of claim 10 wherein the catalyst additionally comprises one or more oxides of a promoter metal selected from the group consisting of Sc, Y, La, rare earth, Mo, W, Ca, Mg, V, Cr, Co, Ni, Mn, Cu, Zn, Cd, Al, Sn, Bi and mixtures thereof with one or more of a promoter metal-containing compound being combined with the iron-containing compound and the potassium-containing compound.

17. The process of claim 10 wherein the promoter metal is selected from Ca, Mg, Mo, W, Ce and mixtures thereof.

18. The process of claim 10 wherein in the preparation of the catalyst the calcination takes place at a temperature ranging from about 750° C. to about 1000° C.

* * * * *